US009050259B2

(12) United States Patent
Shah et al.

(10) Patent No.: US 9,050,259 B2

(45) Date of Patent: Jun. 9, 2015

(54) POWDER COSMETIC COMPOSITION

(75) Inventors: Arvind N. Shah, Suffern, NY (US); Raheel Khan, Franklin Park, NJ (US); Leona Giat Fleissman, Ridgewood, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 11/949,240

(22) Filed: Dec. 3, 2007

(65) Prior Publication Data

US 2009/0142382 A1 Jun. 4, 2009

(51) Int. Cl.

| | |
|---|---|
| ***A61K 8/02*** | (2006.01) |
| ***A61K 8/31*** | (2006.01) |
| ***A61K 8/26*** | (2006.01) |
| ***A61K 8/81*** | (2006.01) |
| ***A61K 8/891*** | (2006.01) |
| ***A61K 8/92*** | (2006.01) |
| ***A61Q 1/10*** | (2006.01) |

(52) U.S. Cl.

CPC ... *A61K 8/31* (2013.01); *A61K 8/26* (2013.01); *A61K 8/8111* (2013.01); *A61K 8/891* (2013.01); *A61K 8/922* (2013.01); *A61K 8/927* (2013.01); *A61Q 1/10* (2013.01); *A61K 8/022* (2013.01)

(58) Field of Classification Search

None

See application file for complete search history.

(56) References Cited

U.S. PATENT DOCUMENTS

| | | | | |
|---|---|---|---|---|
| 4,147,750 | A * | 4/1979 | Geria et al. | 264/255 |
| 4,414,200 | A | 11/1983 | Murphy et al. | |
| 4,724,138 | A | 2/1988 | Duffy et al. | |
| 4,822,603 | A | 4/1989 | Farris et al. | |
| 4,832,944 | A | 5/1989 | Socci et al. | |
| 5,197,814 | A | 3/1993 | Lombardi et al. | |
| 5,340,569 | A | 8/1994 | Elliott et al. | |
| 5,482,547 | A | 1/1996 | Bugnon et al. | |
| 5,688,831 | A | 11/1997 | El-Nokaly et al. | |
| 5,882,662 | A | 3/1999 | Pahlck et al. | |
| 6,083,516 | A * | 7/2000 | Curtis et al. | 424/401 |
| 6,471,950 | B1 | 10/2002 | Farer et al. | |
| 6,696,049 | B2 | 2/2004 | Vatter et al. | |
| 6,972,129 | B1 | 12/2005 | Ogawa et al. | |
| 2002/0028221 | A1 | 3/2002 | Miura et al. | |
| 2004/0091435 | A1 | 5/2004 | Shefer et al. | |
| 2005/0238596 | A1 | 10/2005 | Imai | |
| 2005/0255136 | A1 | 11/2005 | Fleissman et al. | |
| 2006/0228314 | A1 * | 10/2006 | Patil et al. | 424/64 |
| 2007/0134180 | A1 | 6/2007 | Simard et al. | |
| 2007/0134304 | A1 | 6/2007 | Aubrun-Sonneville et al. | |

FOREIGN PATENT DOCUMENTS

| | | | |
|---|---|---|---|
| DE | 3437989 | C1 | 4/1986 |
| EP | 1593366 | A1 | 11/2005 |
| JP | H09295914 | A | 11/1997 |
| JP | H1087471 | A | 4/1998 |
| JP | 2001213730 | A | 8/2001 |
| JP | 2002275034 | A | 9/2002 |
| JP | 2002284642 | A | 10/2002 |
| JP | 2004217567 | A | 8/2004 |
| JP | 2004300039 | A | 10/2004 |
| JP | 2004-346018 | A2 | 12/2004 |
| JP | 2004359552 | A | 12/2004 |
| JP | 2005023047 | A | 1/2005 |
| JP | H06-172125 | A2 | 6/2006 |
| JP | H04-202110 | A2 | 8/2006 |
| JP | 2005248971 | A | 9/2006 |
| JP | H06-284926 | A2 | 10/2006 |
| WO | 02/03950 | A2 | 1/2002 |

OTHER PUBLICATIONS

Michalun et al. in Milady's Skin Care and Cosmetic Ingredients Dictionary, Milady Publishing 1994.*

Dow Corning in Dow Coming AMS-C30 Cosmetic Wax. Product Information Sheet (www3.dowcorning.com/DataFiles/090007c88002052d.pdf), Sep. 2005.*

Microease Technical Data Sheet (www.micropowders.com/personalcare/products/TDS/microease.pdf), Aug. 1999.*

Dow Corning. Dow Coming AMS-C30 Cosmetic Wax. Product Information Sheet, Sep. 2005, retrieved from the Internet http://www3.dowcorning.com/DataFiles/090007c88002052d.pdf.

* cited by examiner

*Primary Examiner* — Dennis Heyer

*Assistant Examiner* — Daniel M Podgorski

(74) *Attorney, Agent, or Firm* — David M. Joyal; Joan M. McGillycoddy

(57) ABSTRACT

Methods for preparing a solid powder cosmetic composition comprise heating a wax component and one or more cosmetic powders at a temperature sufficient to melt the wax, and subsequently cooling the mixture to provide a solid composition comprising a wax matrix having particulate materials homogenously dispersed therein.

17 Claims, 2 Drawing Sheets

POWDER COSMETIC COMPOSITION

FIELD OF INVENTION

The present invention relates generally to powder cosmetic compositions. More particularly, the invention relates to powder cosmetic products formed by heating a mixture of wax and powder to melt the wax, and subsequently allowing the wax to re-solidify.

BACKGROUND OF INVENTION

Conventional powder cosmetic products are typically in the form of a pressed powder cake. Compaction of the powder is necessary to provide sufficient physical cohesion so that the powder cosmetic products can be in the form of a portable compact desired by consumers. However, powder cakes tend to have weak structures because they generally do not incorporate a continuous structural component and are therefore poorly self-supporting. Notably, conventional powder cosmetic products (i.e., powder cakes) are fragile and tend to flake and/or crumble and readily break or crack upon impact. For example, the conventional product is likely to break or crack when dropped by a consumer, resulting in a loss of product usefulness. Traditionally, wet (esters and oils) and dry binders have been incorporated into pressed powders to allow for a stronger cake. However, these binders together with oils from the skin and pressure applied during normal use results in a glazing effect, which is the formation of glossy, hardened aggregates on the surface of the powder cosmetic product. Glazing reduces "payoff" of the powder cosmetic product such that the remaining powder cosmetic becomes essentially unusable by the consumer and is therefore wasted.

The conventional method of preparing a powder cosmetic product is by compressing cosmetic powders with a strong compressive force (e.g., 1000 psi or greater) to obtain pressed powders, or a powder cake. As a consequence of the strong compressive force required to obtain a powder cake, the pressed powders cannot incorporate pressure sensitive components, which would not withstand compaction and consequently lose their functionality.

Representative of the conventional approach to preparing pressed powdered cosmetics is JP Patent Publication 2004-217567, the disclosure of which is incorporated herein by reference. That publication describes a solid powdery eye shadow comprising (a) a powder, provided that the content of a plate-like powder in the whole powder is at least 70 mass % and that the content of flake-like salicylic anhydride in the whole plate-like powder is 5-80 mass %; (b) 1-10 mass % of a hydrocarbon wax powder; and (c) 10-20 mass % of an oily component which is pasty and/or liquid at room temperature. The solid powdery eye shadow is formed by pressing components (a)-(c) into a metal dish.

Alternatively, the ingredients of a powder cosmetic product can be mixed with a solvent and placed in a mold. The solvent is evaporated from the molded mixture to produce a powder cake. An example of an evaporated powder cake is described in U.S. Pat. No. 4,414,200 ("the '200 patent"), the disclosure of which is incorporated by reference. The '200 patent provides a powder stick composition for topical application produced by incorporating an active ingredient, a finely divided inert filler, and a fatty alcohol with siloxane to form a slurry. Thereafter, the slurry is molded and a major portion of the siloxane is evaporated from the cosmetic composition. However, because a shear force is required to blend the powder and solvent mixture, the pressed powders also cannot incorporate shear sensitive components. In addition, the evaporative process is lengthy and the use of certain solvents (e.g., water) can promote undesirable microbial growth.

There is a need in the art for powder cosmetic products that overcome one or more of the foregoing deficiencies of conventional powder cosmetic products and which provides products having heretofore unobtainable advantages. It is therefore an object of the invention to provide powder cosmetic products with improved physical strength so that unique 3-dimensional shapes of powder cake can be incorporated, while providing optimal payoff during use. It is a further object of the invention to provide powder cosmetic products with an improved useable life-span and resistance to glazing effects from repeated use. It is yet another object of the invention to provide powder cosmetic products capable of incorporating a broad range of functional ingredients such as pressure sensitive and/or shear sensitive components.

SUMMARY OF INVENTION

In accordance with the foregoing objectives and others, the present invention overcomes the deficiencies associated with the prior art by providing powder cosmetic products comprising a wax network, formed by heating a mixture of wax and powder to melt the wax, and subsequently allowing the wax to re-solidify, and methods for making the same. The compositions and methods of the invention do not require the application of a strong compressive force or the addition of a volatile solvent to achieve a self-supporting structure. In addition, the compositions of the inventions are durable and resistant to breaking and/or cracking upon impact while maintaining desirable transferability and payoff for cosmetic use. Further, the inventive compositions and method permit a broad range of functional ingredients, such as shear and pressure-sensitive components, to be included.

In one aspect of the invention, a method for preparing a solid cosmetic composition is provided which comprises forming a mixture comprising wax and one or more cosmetic powders, heating the mixture to melt the wax, and subsequently cooling the mixture to form a solid composition. It is believed that by melting the wax, a more continuous network or matrix is formed than when the wax is simply compressed, and thus the overall structure of the product is more robust and resistant to cracking, flaking, breaking etc. Further, the melting step assures that localized clumps of wax and/or powder are substantially avoided, thereby improving the texture and payoff of the product.

In the preferred practice, the method comprises: (a) forming a mixture comprising: (i) wax particles) typically having a median particle size of less than about 30 microns, (ii) a first powdered material having a median particle size less than about 50 microns, and (iii) a second powdered material having a median particle size of at least about 50 microns to about 300 microns; (b) heating the mixture to a temperature sufficient to melt the particles of wax; and (c) cooling the molten wax to a solid state. The first and second powdered materials may be independently selected from any cosmetically useful powder, including without limitation, colorants, fillers, pigments, pearlescent agents, and combinations thereof. In some embodiments, the mixture may further comprise an oil component which also acts as a binder and may serve as an emollient in the finished product. In other embodiments, the mixture may further comprise an inorganic clay, which becomes homogenously dispersed within the cooled wax matrix and which is capable of forming a lattice gel with the oil.

Compositions prepared by the inventive method are also provided.

These and other aspect of the invention will be better understood by reference to the following detailed description, including the figures and appended claims.

DETAILED DESCRIPTION

Figure 1:
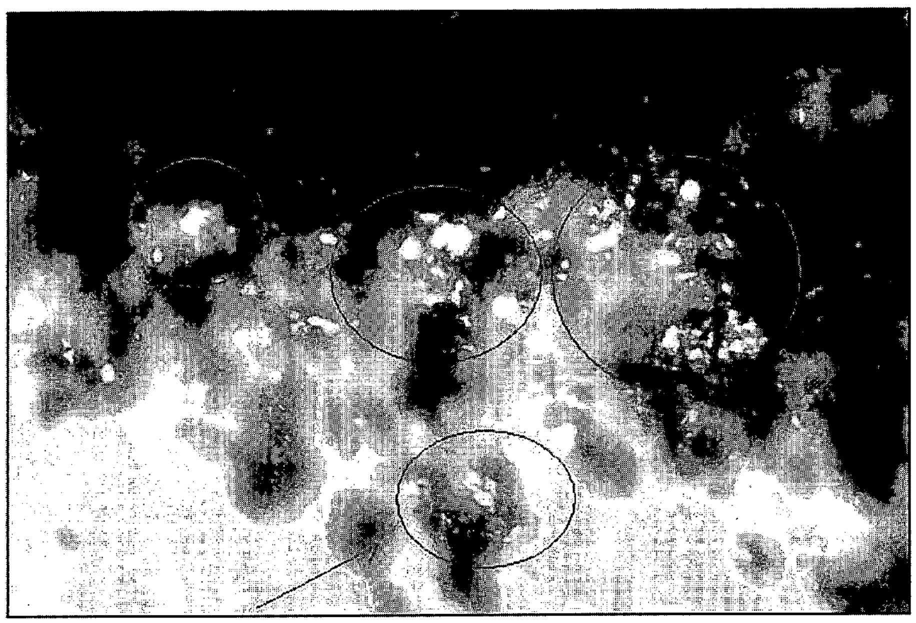
FIG. 1 is a microscopy image of a solid powder cosmetic composition prepared according to the methods of the invention, showing small region of crystalline wax filling the interstices between particulate components.

In the following description of the invention, it is to be understood that the terms used herein have their ordinary and accustomed meanings in the art, unless otherwise specified. All weights percentages referred to herein are given in terms of "% by weight" of the total composition, unless otherwise indicated. All particle sizes referred to herein are given in terms of the median particle size on a volume basis.

The present invention is founded, in part, on the discovery that the physical properties of powder cosmetic products are improved by including therein a wax matrix which is solidified from the molten state in the presence of the powder components. The inventive cosmetic products exhibits a number of superior physical properties as compared to conventional powder cosmetic products (e.g., pressed powder compositions), including resistance to cracking, flaking, or breaking, delivering excellent payoff, and resistance to glazing. Further, because compressive forces are not required to form the products, the inventive methods permit the inclusion of pressure and/or shear sensitive components, such as microcapsules, soft beads, and the like. The solid cosmetic compositions are semi-rigid and moldable to a number of three-dimensional shapes, providing aesthetically pleasing and functional forms that are difficult or impossible to achieve with conventional powder cosmetic products.

The method of the invention generally comprises forming a mixture comprising a wax component and one or more cosmetic powders, heating the mixture to melt the wax, and subsequently cooling the mixture to form a solid composition.

There is essentially no limitation on the selection of the wax component. The wax component may be a single wax or may comprise a combination of waxes. Any wax compatible with a cosmetic product is contemplated to be suitable, including without limitation natural, mineral and/or synthetic waxes.

Natural waxes are those of animal origin, including without limitation beeswax, spermaceti, lanolin, and shellac wax, and those of vegetable origin, including without limitation carnauba, candelilla, bayberry, sugarcane wax, and the like. Natural waxes may also include polycosanols. Mineral waxes contemplated to be useful include, without limitation ozokerite, ceresin, montan, paraffin, microcrystalline, petroleum, and petrolatum waxes. Synthetic waxes include, for example, Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated). Commercially available ethylene-α-olefin copolymer waxes include those sold under the tradename PETROLITE® Copolymers (Baker Hughes Incorporated). Synthetic waxes also include, for example, polyethylene glycols such as PEG-18, PEG-20, PEG-32, PEG-75, PEG-90, PEG-100, and PEG-180 which are sold under the tradename Carbowax® (The Dow Chemical Company). Other suitable waxes are described in Japanese Patent Publication 2004-217567, the disclosure of which is incorporated herein by reference.

The wax is preferably, but not necessarily, one which is not compatible with the cosmetic powder(s) and which resists binding thereto in order to improve the payoff of the product.

Preferably, the wax will be selected from silicone wax, carnauba wax, beeswax, synthetic wax, microcrystalline wax, polyethylene wax, or combinations thereof. More preferably, the wax component will comprise a polydimethylsiloxane with a high molecular weight hydrocarbonalkyl, such as the wax having the INCI name $C_{30-45}$ alkyl methicone (and) $C_{30-45}$ olefins. The wax preferably is sufficiently brittle such that it can be comminuted to small particle sizes by milling or the like, without melting during the milling process. The milled wax is preferably a smooth, soft powder.

Typically, the wax will have a melting point between about 30° C. and about 140° C., more typically between about 40° C. and about 100° C. In various embodiments, the wax component will comprise at least one wax having a melting temperature between about 50° C. and about 90° C., between about 60° C. and about 80° C., and preferably about 70° C. Table 1 provides several suitable waxes arranged by melting point or melting range.

TABLE 1

| Wax | Melting Point (° C.) |
|---|---|
| acrawax | 140 |
| microcrystalline petroleum wax | 99 |
| linear polyethylene wax | 95 |
| stearone | 89 |
| castor wax | 86 |
| montan wax | 82-95 |
| lignite wax | 82-95 |
| ouricouri wax | 81-84 |
| carnauba wax | 78-85 |
| rice bran wax | 77-86 |
| shellac wax | 74-78 |
| esparto wax | 73 |
| ozokerite wax | 72 |
| jojoba wax | 70 |
| candelilla wax | 68-73 |
| ceresin wax | 67-71 |
| beeswax | 62-64 |
| castor wax | 60 |
| sugarcane wax | 60 |
| stearyl alcohol | 59 |
| hard tallow | 57-60 |
| cetyl alcohol | 56 |
| petrolatum | 54 |
| glyceryl monostearate | 54-56 |
| Japan wax | 53 |
| silicone waxes | 53-75 |
| paraffin wax | 50-60 |
| lanolin alcohol | 45-60 |
| bayberry wax | 45 |
| cetyl palmitate | 43-53 |
| lanolin | 38-42 |
| illipe butter | 34-38 |
| cocoa butter | 31-35 |

It will be understood that the melting points and ranges provided in Table 1 are merely representative of typical values for each wax and wide variation in the melting point or melting point range may be observed from sample to sample depending on the source and purity of the wax. It is within the skill in the art to determine the melting point or melting point range of any given wax sample. Melting points may be determined, for example, by drop melting point according to ASTM D127, incorporated by reference herein, and/or ring-and-ball softening point according to ASTM D36, incorporated by reference herein. The mixture of wax and powdered material is heated to the melting temperature of the wax, preferably above the melting temperature of the wax, for a time sufficient to melt substantially all of the wax.

While it is contemplated that the wax may be added to the mixture in the molten state, it is preferred to add the wax in solid, particulate form. In the preferred practice of the invention, the wax particles will have a small median particle size such that they are well dispersed with the powdered components. The wax particles are mixed with other powders in the formulation and passed through mechanical milling so that all resulting particles have a tighter mean range to ensure homogeneity. In one embodiment, the wax component will have a median particle size less than about 30 microns, more typically less than about 25 microns, preferably less than about 20 microns, and more preferred still less than about 15 microns. Superior results have been obtained where the particle size of the wax is less than about 12.5 microns, including a representative embodiment wherein the median particle size of the wax is about 10 microns. However, it is contemplated that wax particles sizes of less than about 7.5 microns, less than about 5 microns, or even less than about 2.5 microns will also be useful in the practice of the invention.

The wax will typically comprise from about 1 to about 30% by weight of the mixture. In one embodiment, wax will typically comprise from about 3 to about 25% by weight of the mixture, and preferably from about 5 to about 15% by weight of the mixture.

The mixture will also comprise a particulate component which may comprise one or more cosmetic powders. Preferably, the particulate component comprises at least two cosmetic powders, each of which has a different median particle size. Thus, the preferred particulate components according to the invention will comprise a bi-modal or multi-modal distribution of particles. The powdered materials are any powdered materials useful in cosmetic products. The powders may comprise any shape and size particles including, for example, spherical, amorphous, and platelet shaped particles.

In one embodiment, the particulate component comprise a first cosmetic powder of small median particle size and a second cosmetic powder of large median particle size. The first cosmetic powder will typically have a median particle size greater than 0.01 microns and less than about 50 microns. In other embodiments, the first powder will have a median particle size less than about 45 microns, less than about 35 microns, less than about 30 microns, less than about 25 microns, less than about 20 microns, or less than about 17.5 microns, less than about 15 microns, less than about 12.5 microns, less than about 10 microns, less than about 7.5 microns, less than about 5 microns, less than about 2.5 microns, less than about 1 micron, or less than about 0.5 microns.

The particulate phase preferably also comprises a second powdered material having a median particle size greater than the size of the first powdered material. Typically, the second powder will have a median particle size of at least about 50 microns. In other embodiments, the second powder will have a particle size of at least about 75 microns, at least about 100 microns, at least about 125 microns, or at least about 150 microns. The best results will be obtained where the particle size of the second powder is no greater than about 300 microns since such very large particles may result in an undesirable coarseness in the cosmetic product. Usually, the second powdered material will have a particle size no greater than about 200 microns.

The bi-modal or multi-modal distribution of particles, having varying shapes and sizes, permits dense packing with little or no pressure, due to the reduced void space between particles as compared to arrangements with uniformly sized and shaped particles. Further, the bi-modal or multi-modal distribution of particles improves the payoff of the solid cosmetic composition since uniform particles tend to form too strong of networks which resist shear force, and consequently diminish payoff during normal cosmetic use.

Where a color cosmetic is desired, the cosmetic powders of the mixture may comprise one or more colorants. The colorant may comprise from about 0.1 to about 80% by weight of the mixture. Preferably, the colorant will comprise from about 0.5 to about 70% by weight of the mixture. More preferably, the colorant will comprise from about 1 to about 60% by weight of the mixture.

Suitable colorants, including pigments, pearlescent agents, lakes, and dyes, are well known in the art and are disclosed in the C.T.F.A. Cosmetic Ingredient Handbook, First Edition, 1988, the contents or which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\beta$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. The colorants may be surface modified with, for example, fluoropolymers, to adjust one or more characteristics of the colorant as described in, for example, U.S. Pat. Nos. 6,471,950, 5,482,547, and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference. The compositions may also include glittering agents.

The cosmetic powder may also include various fillers and/or additional components. The solid cosmetic composition of the invention may include from 0 to 80 weight % filler. Preferably, the solid cosmetic composition may include from 5 to 70 weight % filler. More preferably, the solid cosmetic composition may include from 10 to 60 weight % filler. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like. Functional agents may be, for example, insect repellants, UV absorbers, UV blockers, antiperspirants, moisturizers, conditioners, tooth whiteners, and the like.

Additional colorant/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly (ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, the disclosure of which is hereby incorporated by reference.

The solid cosmetic composition of the present invention may include one or more wet binders, such as oils and the like. By "wet" binder is meant a liquid composition, rather than an aqueous composition, as the mixture is preferable free of water and other volatile solvents. The solid cosmetic composition may comprise from 1 to 30% by weight, preferably from 3 to about 25% by weight, and more preferably from about 5 to about 15% by weight wet binder (e.g., oils). The oils is preferably non-volatile and may be selected from the group consisting of esters, silicone oils, hydrocarbon oils, polyols (e.g., glycerin) and certain polymers, such as polyurethanes, acrylates and the like. In a preferred embodiment, emollients may be added to the solid cosmetic composition of the present invention without significantly reducing the powder cosmetic product's payoff. Suitable oils are also described in Japanese Patent Publication 2004-217567, the disclosure of which is incorporated herein by reference.

Ester oils include any non-polar or low-polarity ester, including isostearyl neopentonoate, isostearyl hydroxystearate, octyldodecyl stearoyl stearate, glyceryl esters, coco-caprylate/caprate, caprylic/capric triglyceride, stero esters, PPG-1 isoceteth-3 acetate, and the like. Special mention may be made of those fatty acid esters commonly used as emollients in cosmetic formulations. Such esters will typically be the etherification product of an acid of the form $R_1(COOH)_{1-2}$ with an alcohol of the form $R_2(OH)_{1-3}$ where $R_1$ and $R_2$ are each independently linear, branched, or cyclic hydrocarbon groups, optionally containing unsaturated bonds, and having from 1 to 30 carbon atoms, preferably from 2 to 30 carbon atoms, and more preferably, from 3 to 30 carbon atoms, optionally substituted with one or more functionalities including hydroxyl, oxa, oxo, and the like. Preferably, at least one of $R_1$ and $R_2$ comprises at least 10, and more preferably, at least 15, 16, 17, or 18 carbon atoms, such that the ester comprises at least one fatty chain. The esters defined above will include, without limitation, the esters of mono-acids with mono-alcohols, mono-acids with diols and triols, di-acids with mono-alcohols, and tri-acids with mono-alcohols.

Suitable fatty acid esters include, without limitation, butyl acetate, butyl isostearate, butyl oleate, butyl octyl oleate, cetyl palmitate, ceyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyidodecyl myristate or lactate, di(2-ethylhexyl) succinate, tocopheryl acetate, and the like.

Other suitable esters include those wherein $R_2$ comprises a polyglycol of the form H—(O—CHR*—CHR*)$_n$— wherein R* is independently selected from hydrogen or straight chain alkyl, including methyl and ethyl, as exemplified by polyethylene glycol monolaurate.

Salicylates and benzoates are also contemplated to be useful esters in the practice of the invention. Suitable salicylates and benzoates include esters of salicylic acid or benzoic acid with an alcohol of the form $R_3OH$ where $R_3$ is a linear, branched, or cyclic hydrocarbon group, optionally containing unsaturated bonds, and having from 1 to 30 carbon atoms, preferably from 6 to 22 carbon atoms, and more preferably from 12 to 15 carbon atoms. Suitable salicylates include, for example, octyl salicylate and hexyldodecyl salicylate, and benzoate esters including $C_{12-15}$ alkyl benzoate, isostearyl benzoate, hexyldecyl benzoate, benzyl benzoate, and the like.

Other suitable esters include, without limitation, polyglyceryl diisostearate/IPDI polymeric copolymer, triisostearoyl polyglyceryl-3 dimer dilinoleate, polyglycerol esters of fatty acids, and lanolin, to name but a few.

The oil may also be a non-volatile silicone oil. Suitable silicone oils include linear or derivatives of the cyclic silicones such as polyalkyl- or polyarylsiloxanes, optionally comprising alkyl or alkoxy groups having from 1 to 10 carbon atoms. Representative silicone oils include, for example, capryl lmethicone, decamethylcyclopentasiloxane, decamethyltetrasiloxane, diphenyl dimethicone, dodecamethylcyclohexasiloxane, dodecamethylpentasiloxane, heptamethylhexyltrisiloxane, heptamethyloctyltrisiloxane, hexamethyldisiloxane, methicone, methyl-phenyl polysiloxane, octamethylcyclotetrasiloxane, octamethyltrisiloxane, perfluorononyl dimethicone, polydimethylsiloxanes, and combinations thereof.

The silicone oil will typically, but not necessarily, have a viscosity of between about 50 and about 3,000 centistokes (cst), preferably between 100 and 1,000 cSt measured at 25° C.

In one embodiment, the silicone oil comprises phenyl groups, as is the case for the silicone oil methylphenylpolysiloxane, INCI name diphenyl dimethicone, commercially available from Shin Etsu Chemical Co under a variety of tradenames including F-5W, KF-54 and KF-56. Diphenyl dimethicones have good organic compatibility and impart film-forming characteristics to the product. In one embodiment, the silicone oil will have a refractive index of at least 1.3, preferably at least 1.4, more preferably at least 1.45, and more preferred still at least 1.5, when measured at 25° C. Another suitable phenyl-functionalized silicone oil has the INCI name phenyltrimethicone and is sold under the trade name "DC 556" by Dow Corning. DC 556 has a refractive index of about 1.46.

In one embodiment of the invention, the silicone oil is a fluorinated silicone, preferably a perfluorinated silicone (i.e., fluorosilicones). The preferred fluorosilicone is a fluorinated organofunctional silicone fluid having the INCI name perfluorononyl dimethicone. Perfluorononyl dimethicone is commercially available from Pheonix Chemical under the trade name Pecosil®.

The compositions may also comprise hydrocarbon oils, preferably a non-volatile hydrocarbon oil. Exemplary hydrocarbon oils are straight or branched chain paraffinic hydrocarbons having from 20 to 80 carbon atoms, including but not limited to tetradecane, tridecane, and the like. Preferred hydrocarbon oils are highly branched aliphatic hydrocarbons, including $C_{20-40}$ isoparaflins and the like. Special mention may be made of the isoparaffins having the INCI names isohexadecane and isoeicosane.

Suitable hydrocarbon oils are commercially available from Presperse (Somerset, N.J.) under the Permethyl® line of oils, including without limitation Permethyl® 98B (Polyisobutene/Isododecane), Permethyl® 216C ($C_{18-21}$ Alkane/$C_{13-16}$ Isoparaffin), Permethyl® 101A (Isohexadecane), Permethyl® 102A (Isoeicosane), Permethyl® 104A (Polyisobutene), Permethyl® 222C ($C_{13-15}$Alkane/$C_{12-20}$ Isoparaffin), Permethyl® 105A (Polyisobutene), Permethyl® 246C ($C_{18-21}$Alkane/Polyisobutene), Permethyl® 284C ($C_{15-19}$Alkane/$C_{12-14}$Isoparaffin/Polyisobutene), and Permethyl® 296C ($C_{12-14}$Isoparaffin/$C_{18-21}$Alkane).

Also suitable as hydrocarbon oils are polyalphaolefins, typically having greater than 20 carbon atoms, including $C_{24-28}$ olefins, $C_{30-45}$ olefins, hydrogenated polyisobutene, hydrogenated polydecene, polybutene, mineral oil, pentahydrosqualene, squalene, squalane, and the like. The hydrocarbon oil may also comprise higher fatty alcohols, such as oleyl alcohol, octyldodecanol, and the like.

Other suitable oils include without limitation castor oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, and combinations thereof.

Dry binders are also contemplated to be useful according to the present invention, although they are strictly optional. When present, the dry binder will typically comprise from 0.01 to 15% weight of the mixture, preferably from about 1 to about 12% by weight, and more preferably, from about 2 to about 9% by weight of the mixture. Dry binders include, without limitation, zinc stearate and kaolin.

The composition according to the invention may also incorporate a lattice gel. Preferably, the lattice gel is homogenously dispersed, or evenly distributed, within the solid cosmetic composition. The combination of a continuous, interconnected matrix of wax and a lattice gel provides a solid cosmetic composition that is capable of binding the cosmetic powder and maintaining a strong structure of the solid cosmetic compositions at elevated temperatures, and preferably even at temperatures above the melting point of the wax. The lattice gel network may comprise inorganic clays, such as smectite clay, bentone clay, and the like. In one embodiment, the lattice gel network may be formed with, for example, smectite clay and oils, as described in, for example, U.S. Pat. No. 5,882,662, the contents of which are hereby incorporated by reference. As will every ingredient, the inorganic clay, when present, is added to the mixture prior to heating.

The solid cosmetic composition may optionally include preservatives. When present, the preservatives will include from about 0.01 to about 5% by weight, typically about 0.05 to about 4% by weight, and preferably about 0.1 to about 3% by weight % of the mixture.

The compositions of the invention may optionally comprise other active and inactive ingredients typically associated with cosmetic and personal care products, including, but not limited to, excipients, fillers, emulsifying agents, antioxidants, surfactants, film formers, chelating agents, gelling agents, thickeners, emollients, humectants, moisturizers, vitamins, sodium ascorbyl/cholesteryl phosphate, minerals, viscosity and/or rheology modifiers, sunscreens, keratolytics, depigmenting agents, retinoids, hormonal compounds, alpha-hydroxy acids, trioxaundecanedioic acid, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. Although, the selection and amounts of such additional ingredients should be judiciously selected so as not to adversely impact the integrity of the percolating wax network or the payoff of the product.

The mixture of the wax component and powder component and optionally other ingredients such as oils, etc., are preferably blended prior to heating to form a substantially homogenous admixture. The components may be blended by any suitable means. The wax component may be mixed with the cosmetic powder(s), and optionally additional ingredients, using any suitable means. Preferably, the wax particles may be mixed with the cosmetic powder in the substantial absence of volatile solvents, by which is meant that the mixture comprises less than about 2% by weight volatile solvent and preferably less than about 1% by weight volatile solvent. In the preferred practice, the mixture is free of volatile solvents.

The mixture may be placed into any suitable container, preferably a mold, and heated to a temperature above the melting point of the wax particles for a time sufficient to melt at least a predominate portion, but preferably all, of the wax. Upon heating the mixture to a temperature sufficient to melt the particles of wax, the wax transitions into a viscous or liquid phase. Preferably, mixture is not agitated or stirred during heating. Ideally, the melted wax should flow into the void spaces between particles of cosmetic powder and fill at least a portion of the spaces, without any agitation or stirring. In other words, the melted wax, seeps through the space between, or "percolates" through, the cosmetic powder particles. Thus, the resulting wax matrix may be referred to as a percolating network.

The mixture may be heated using any suitable means. In one embodiment, the powder mixture is subjected to microwave heating. Microwave heating may have the advantage that the mixture is heated evenly from the inside outward to achieve rapid and uniform melting of the wax. When microwave heating is employed, it is preferred that the wax be at least somewhat polar, as non-polar waxes typically will not melt effectively in the microwave. In another embodiment, the mixture is heated in a convection or similar oven. In the preferred practice, the powder mixture is heated in a heat tunnel.

In one particular embodiment, where the powder cosmetic compositions comprises wax having a melting point of about 70° C., such as, for example, $C_{30-45}$ Alkyl Methicone (and) $C_{30-45}$ Olefins, the powder mixture may be heated to a temperature from about 70° C. to about 110° C. for a period from about 10 to about 90 minutes. Preferably, the powder mixture may be heated to a temperature from about 75° C. to about 100° C. for a period from about 20 to about 60 minutes. More preferably, the powder mixture may be heated to a temperature from about 80° C. to about 90° C. for a period from about 30 to about 45 minutes.

A compressive force is typically applied to the solid cosmetic composition prior to the heating step to improve the packing of the cosmetic powder and wax particles and reduce void space between particles. In various embodiments of the present invention, the compressive force may be less than 500 psi, less than 400 psi, less than 300 psi, less than 200 psi, less than 100 psi, less than 50 psi, or less than 25 psi. However, the compressive force should be insufficient to affect pressure-sensitive components.

After the wax has been thoroughly melted, the composition is cooled, preferably to room temperature, during which time the wax solidifies. It is believed that the solidified wax forms a substantially continuous phase comprising an interconnected matrix binding the cosmetic powder to form a solid, semi-rigid cosmetic composition having any desired three-dimensional shape, depending on the shape of the mold in which the mixture was heated. Suitable shapes may include geometric shapes or irregular shapes. Geometric shapes include, domes, pyramids, hemispheres and the like. Irregular shapes include but are not limited to, diamond, gemstones, sharp bevels, waves, and the like.

Referring to FIG. 1, a microscopy image of powder cosmetic product prepared according to the inventive method is shown. Within the circled regions of FIG. 1, white spots are clearly visible which represent crystalline wax “percolating” through the interstices between closely packed particulates. These crystalline regions are small and relatively uniform in size and distribution, which is in contrast to a conventional pressed powder cosmetic which is expected to show regions of substantial inhomogeneity characterized by localized clusters of wax and clusters of particulates since, in the absence of heat, the wax cannot percolate throughout and fuse the particles into a coherent mass.

In contrast to conventional processes of making powder cosmetic products, the method for preparing the solid cosmetic products of the present invention does not require the application of a strong compressive force or a shear force. Therefore, the method of the present invention is compatible with pressure sensitive and/or shear sensitive components in the mixture. For example, soft beads and microspheres can provide additional functional benefits to the product, such as changing color or releasing contents upon application of pressure.

While the foregoing description relates to preferred compositions according to the invention, it is contemplated that any powder cosmetic composition which comprises wax will benefit from the surprising discovery that heating the product to melt the wax will provide a more extensive matrix on cooling than achievable solely by compression techniques.

The compositions according to the invention may be useful in a variety of cosmetic and personal care products, including without limitation, eye shadow, eye liner, eye pencils, concealer, blush, face powders, foundations, powder lipstick, body powder sticks, and other powder cosmetic products.

EXAMPLE I

Eyeshadow

An exemplary powder eyeshadow composition of the present invention having an interconnected matrix and cosmetic powder having a multi-modal distribution of particles is provided in Table 2.

TABLE 2

| COMPONENTS (INCI Name) | (Wt. %) |
|---|---|
| **Fillers** | |
| Talc | 13.15 |
| Sericite | 8 |
| Polymethyl methacrylate (having spherical particles) | 2.5 |
| Bismuth oxychloride | 1.5 |
| Corn starch modified | 5 |
| Vinyl Dimethyl/methyl silsesquixane crosspolymer | 3 |
| Total Fillers | 33.15 |
| **Wax** | |
| $C_{30-45}$ Alkyl methicone/$C_{30-45}$ Olefin | 7 |
| Total Wax | 7 |
| **Pigments/Pearls** | |
| Iron oxide (mix of black, red and yellow) | 9.25 |
| Carmine | 1 |
| Pearlescents (iron oxide and titanium dioxide coated micas) | 35 |
| Total Pigments/Pearls | 45.25 |
| **Dry Binders** | |
| Zinc stearate | 2 |
| Kaolin | 2 |
| Total Dry Binders | 4 |
| **Wet Binders** | |
| Octyldodecyl stearoyl stearate | 2 |
| Isostearyl Isostearate | 5 |
| Bis-Stearyl Ethylenediamine | 2 |
| Polyglyceryl-3 Dimer Dilinoleate | 1 |
| Total Wet Binders | 10 |
| **Preservatives** | |
| Tetrasodium EDTA | 0.1 |
| Methylparaben | 0.3 |
| Butylparaben | 0.2 |
| Total Preservatives | 0.6 |

The powder cosmetic composition of Table 2 was prepared by mixing the fillers, pigments (excluding the pearlescent agents), binders, and preservatives to form a cosmetic powder pre-mix. A wet pre-mix was prepared by mixing a portion of the wet binders with the wax at a temperature of 85° C. The cosmetic powder pre-mix is combined with the wet pre-mix. The wet premix is sprayed onto the powder premix, combining the two components together. The combination is then processes using a hammer mill. Thereafter, the pearlescent agents and the remaining portion of the wet binders are added and mixed into the combination.

The mixture is then gently pressed into a three dimensional mold and heated in a convection oven at a temperature of 80° C. for about 30 minutes.

EXAMPLE II

Eyeshadow

Another exemplary powder eyeshadow composition of the present invention having an interconnected matrix and cosmetic powder having a multi-modal distribution of particles is provided in Table 3. The eyeshadow may be made using the same process as described above in Example I.

TABLE 3

| COMPONENTS (INCI Name) | Amount (Wt. %) |
|---|---|
| **Fillers/Skin Modifiers** | |
| Talc (having median particle size of 14 to 16 Microns) | 11.95 |
| Nylon Powder (Extra Fine) | 3 |
| Vinyl Dimethyl/methyl silsesquixane crosspolymer | 1.5 |
| Titanium Dioxide (0.03 Microns-USP) | 1 |
| Polyethylene/Dimethiconol Copolymer | 1.5 |
| Polymethyl Methacrylate (having spherical particles) | 2 |
| Silica (Low absorbing) | 0.5 |
| Bismuth Oxychloride (UVR) | 1.5 |
| Sericite | 8 |
| Methyl Methacrylate Crosspolymer | 1 |
| Total Fillers | 31.95 |
| **Wax** | |
| Myristyl Lactate | 0.5 |
| $C_{30-45}$ Alkyl methicone/$C_{30-45}$ Olefin | 7 |
| Bis-Stearyl Erhylenediamine/Neopentyl glycol/ Stearyl hydrogenated Dimer Dilinoleate Copolymer/Antiox. | 2 |
| Total Wax | 9.5 |
| **Colorants** | |
| Carmine 5297 | 0.2 |
| Iron oxide (black) | 3.05 |
| Iron oxide (yellow) | 0.9 |
| Cosmetic Red Oxide | 5.3 |
| Mica-74%/Titanium Dioxide | 20 |
| Chroma-Lite Black #CL4498 | 8 |
| Timiron MP-1001-SuperSheen #017201 | 7 |
| Total Pigments/Pearls | 44.45 |
| **Dry Binders** | |
| Zinc stearate | 4 |
| Kaolin | 1.5 |
| Total Dry Binders | 5.5 |
| **Wet Binders** | |
| Triisostearoyl Polyglyceryl-3 Dimer Dilinoleate | 1 |
| Isostearyl Isostearate | 2 |
| Octyldodecyl stearoyl stearate | 5 |
| Total Wet Binders | 8 |
| **Preservatives** | |
| Tetrasodium EDTA | 0.1 |
| Methylparaben | 0.3 |
| Butylparaben | 0.2 |
| Total Preservatives | 0.6 |

EXAMPLE III

The payoff of a powder cosmetic product prepared according to the invention was compared to the payoff of a conventional pressed powder cosmetic product as a function of wax loading. Samples were prepared according to formulas A-E by either heating to a temperature sufficient to melt the wax or compressing the product in the absence of heat. The wax levels ranged from 5% to 20% by weight, as shown in Table 4.

TABLE 4

| Component | Weight % | | | | |
|---|---|---|---|---|---|
| Formula: | A | B | C | D | E |
| Talc (filler) | 46.0 | 43.5 | 41.0 | 36.0 | 31.0 |
| Nylon (filler) | 3.0 | 3.0 | 3.0 | 3.0 | 3.0 |
| Mica (filler) | 5.0 | 5.0 | 5.0 | 5.0 | 5.0 |
| Vinyl Dimethyl/methyl silsesquixane crosspolymer (filler) | 6.0 | 6.0 | 6.0 | 6.0 | 6.0 |
| Myristal Myristate (wax) | 5.0 | 7.5 | 10.0 | 15.0 | 20.0 |
| iron oxide and titanium dioxide coated micas (pearlescent colorant) | 20.0 | 20.0 | 20.0 | 20.0 | 20.0 |
| Tridecyl Neopentanoate (wet binder) | 15.0 | 15.0 | 15.0 | 15.0 | 15.0 |

Payoff Test Method

This method may be utilized to determined the payoff or transferability of a powder cosmetic composition. This test predicts the ability of the cosmetic composition to be transferred onto an applicator or a finger during normal use of the cosmetic product. The payoff of the product is directly proportional to the amount of cosmetic products removed by application of shear force. Therefore, the payoff may be expressed as a function of the amount of cosmetic products lost following the rub test described herein.

First, weigh the product to determine the initial weight of each the solid cosmetic composition. Then, using circular motion, rub the surface of the cake with a foam tipped applicator or with a finger 50 times. Lastly, weight the product again to determine the amount of cosmetic products removed from the solid cosmetic composition by rubbing. The total weight loss after fifty rubbings is divided by 25 to reflect the fact that the consumer, on average, will rub the applicator twice over the surface of the cake. Thus, the resulting average loss value is representative of the weight of cosmetic transferred to the skin of the consumer during a typical application.

Figure 2:
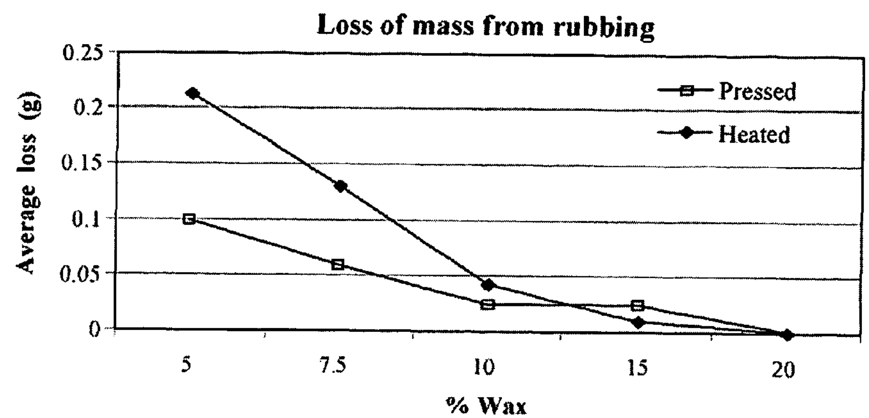
FIG. 2 is a plot of mass loss from rubbing a foam applicator across the surface of a powder cosmetic composition according to the invention compared to a pressed powder cake, plotted as a function of wax content.

The results are shown in FIG. 2 as the amount of mass transferred to the skin as a function of the amount of wax (by weight %) in the powder cosmetic compositions according to the invention (♦) and the conventional pressed product (□). As displayed in the graph, the packing of the baked cosmetic is looser, allowing for an increased payoff compared to the payoff of standard pressed powder with equal levels of wax. This allows a consumer to get a true color and an intense payoff.

EXAMPLE IV

The improved durability of solid cosmetic compositions of the present invention as compared to conventional powder cosmetic compositions was investigated. Two otherwise identical samples of a powder cosmetic composition were prepared. One sample was pressed using conventional techniques at 1000 psi whereas another sample was prepared using the method of the present invention, which includes heating the cosmetic composition to a temperature sufficient to melt the wax particles and cooling said mixture to a thereby provide a percolating wax matrix having homogenously distributed therein cosmetic powder particles.

Drop Test Method

This method may be utilized to determine the durability of a powder cosmetic composition. This test predicts the ability of the cosmetic composition resist breaking or cracking. The undesired tendency of a cosmetic product to break or crack is directly proportional to the amount of cosmetic powders lost when the product is dropped from a particular altitude. Therefore, the breaking and/or cracking of the cosmetic product may be expressed as a function of the amount of cosmetic products lost following the drop test described herein.

First, weight the product to determine the initial weight of each the solid cosmetic composition. Then, drop the solid cosmetic composition from a height approximately 30 inches onto a flat hard surface, in such a manner that it lands flat on its underside, without turning over during its fall. Next, drop the same solid cosmetic composition a second time from approximately a height of 12 inches. Lastly, weight the product again to determine the amount of cosmetic products lost from the two drops. Repeat for four additional times, dropping the solid cosmetic composition from a height of approximately 30 inches and a height of approximately 12 inches and subsequently weighting the cosmetic products.

Figure 3:
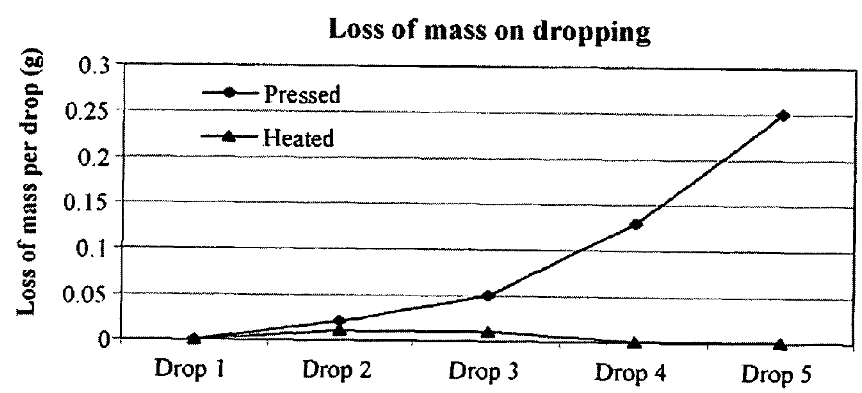
FIG. 3 is a plot of mass loss as a result of dropping from designated heights for a conventional pressed powder cosmetic and a powder cosmetic composition of the present invention.

FIG. 3 illustrates the amount of mass lost as a result of dropping from designated heights for a conventional powder cosmetic and a powder cosmetic composition of the present invention. A conventional powder cosmetic composition is represented with the symbol (♦) and a powder cosmetic composition of the present invention is represented by the symbol (▲). As can be seen, the powder cosmetic composition of the present invention (▲) does not exhibit significant mass loss whereas the conventional powder cosmetic composition (♦) shows a steady increase in the amount of mass lost following each successive drop. Therefore, the powder cosmetic composition of the present invention (♦) is a stronger and more stable structure than the conventional powder cosmetic composition formed by using the conventional technique.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method for preparing a solid color cosmetic composition in the form of a powder cake comprising:

(a) providing a substantially homogenous mixture that is substantially free of volatile solvents, said substantially homogenous mixture comprising:

(i) solid wax particles having a median particle size of less than about 30 microns, (ii) a first powdered material comprising a pigment having a median particle size from about 0.01 microns to less than about 50 microns, and (iii) a second powdered material having a median particle size from about 50 microns to about 300 microns, wherein said second powdered material is selected from colorants, fillers, pigments, pearlescent agents, and binders;

(b) heating said substantially homogenous mixture in the absence of agitation or stirring to a temperature sufficient to melt said wax particles and form a continuous molten network or matrix; and (c) cooling said continuous molten network or matrix to a solid state, wherein said color cosmetic composition is characterized by an increased payoff and enhanced resistance to cracking, flaking, or breaking, as compared to an otherwise identical composition prepared in the absence of heat.

2. The method of claim 1, wherein said wax particles comprise from about 1 to about 30 percent by weight of said mixture.

3. The method of claim 1, wherein said wax particles comprise from about 3 to about 25 percent by weight of said mixture.

4. The method of claim 3, wherein said wax particles comprise from about 5 to about 15 percent by weight of said mixture.

5. The method of claim 1, wherein the wax particles comprise one or more waxes selected from silicone wax, carnauba wax, beeswax, synthetic wax, microcrystalline wax, and polyethylene wax.

6. The method of claim 1, wherein the wax particles comprise $C_{30-45}$ Alkyl Methicone (and) $C_{30-45}$ Olefin (INCI).

7. The method of claim 1, wherein the first powdered material comprises a pigment and the second powdered material comprises mica.

8. The method of claim 1, wherein the mixture further comprises an oil.

9. The method of claim 8, wherein said oil comprises from about 1 to about 30 percent by weight of said mixture.

10. The method of claim 9, wherein said oil comprises from about 3 to about 25 percent by weight of said mixture.

11. The method of claim 10, wherein said oil comprises from about 5 to about 15 percent by weight of the mixture.

12. The method of claim 8, wherein the mixture further comprises an inorganic clay.

13. The method of claim 12, wherein the inorganic clay comprises smectite clay or bentone clay.

14. The method of claim 1, wherein the oil comprises at least one oil selected from the group consisting of ester oils, silicone oils, hydrocarbon oils, and polyols.

15. The method of claim 1, wherein said heating step comprises microwave heating of the mixture.

16. The method of claim 15, wherein said heating step is carried out in a convection oven.

17. The method of claim 15, wherein said heating is carried out in a heat tunnel.

* * * * *